United States Patent
Sugihara et al.

(10) Patent No.: US 7,643,137 B2
(45) Date of Patent: Jan. 5, 2010

(54) DEFECT INSPECTION APPARATUS, DEFECT INSPECTION METHOD AND METHOD OF INSPECTING HOLE PATTERN

(75) Inventors: Mari Sugihara, Shinagawa-ku (JP); Takeo Oomori, Sagamihara (JP); Kazuhiko Fukazawa, Misato (JP)

(73) Assignee: Nikon Corporation, Tokyo (JP)

( * ) Notice: Subject to any disclaimer, the term of this patent is extended or adjusted under 35 U.S.C. 154(b) by 224 days.

(21) Appl. No.: 11/243,425

(22) Filed: Oct. 5, 2005

(65) Prior Publication Data

US 2006/0232769 A1 Oct. 19, 2006

Related U.S. Application Data

(63) Continuation-in-part of application No. 10/805,240, filed on Mar. 22, 2004, now abandoned.

(30) Foreign Application Priority Data

Mar. 26, 2003 (JP) ............................. 2003-085185
Oct. 6, 2004 (JP) ............................. 2004-322905

(51) Int. Cl.
*G01N 21/00* (2006.01)
(52) U.S. Cl. ............... 356/237.2; 356/237.4; 356/237.5
(58) Field of Classification Search ... 356/237.2–237.5; 250/559.41–559.45; 382/141, 147, 145, 382/149; 348/125, 126, 128, 129, 131
See application file for complete search history.

(56) References Cited

U.S. PATENT DOCUMENTS

| | | | | |
|---|---|---|---|---|
| 5,278,012 A | * | 1/1994 | Yamanaka et al. | ............ 430/30 |
| 5,432,607 A | | 7/1995 | Taubenblatt | |
| 5,764,363 A | | 6/1998 | Ooki et al. | |
| 5,777,744 A | | 7/1998 | Yoshii et al. | |
| 5,973,777 A | * | 10/1999 | Nomoto et al. | .......... 356/237.5 |
| 6,018,391 A | * | 1/2000 | Yoshida | ...................... 356/484 |
| 6,594,012 B2 | | 7/2003 | Takeuchi et al. | |
| 6,690,469 B1 | * | 2/2004 | Shibata et al. | .............. 356/369 |
| 2002/0021448 A1 | | 2/2002 | Ishizuka et al. | |
| 2002/0060789 A1 | * | 5/2002 | Fukazawa et al. | ......... 356/237.2 |

FOREIGN PATENT DOCUMENTS

| | | |
|---|---|---|
| JP | A 11-051874 | 2/1999 |
| JP | A-2002-116011 | 4/2002 |
| JP | B2 3618907 | 11/2004 |
| JP | B2 3630852 | 12/2004 |

* cited by examiner

*Primary Examiner*—Gregory J Toatley, Jr.
*Assistant Examiner*—Tri T Ton
(74) *Attorney, Agent, or Firm*—Oliff & Berridge, PLC

(57) ABSTRACT

A defect inspection apparatus for inspecting a defect of a substrate as an object to be inspected comprises an illumination optical system for illuminating the substrate, a receiving optical system for receiving diffracted light from the substrate and a polarizing element provided in either one of the illumination optical system or the receiving optical system.

8 Claims, 7 Drawing Sheets

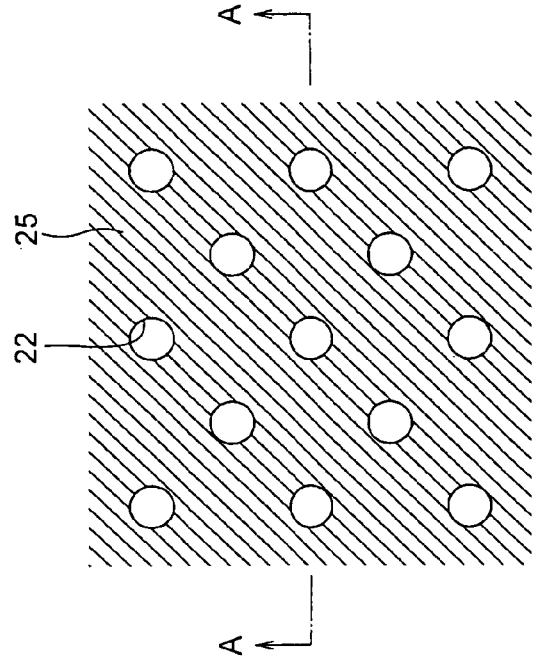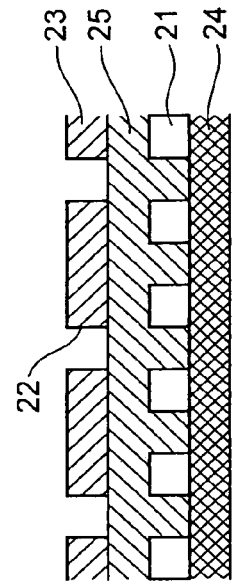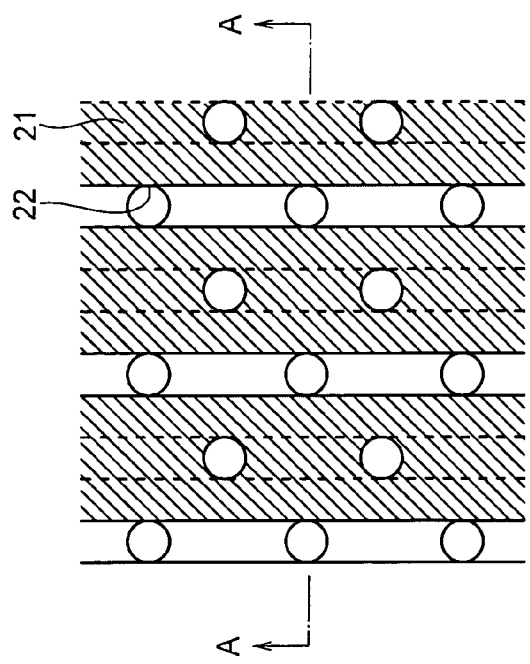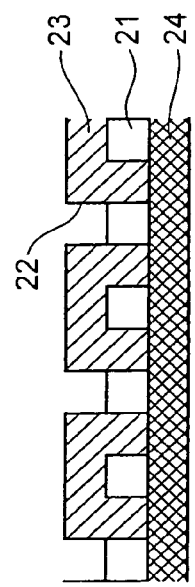

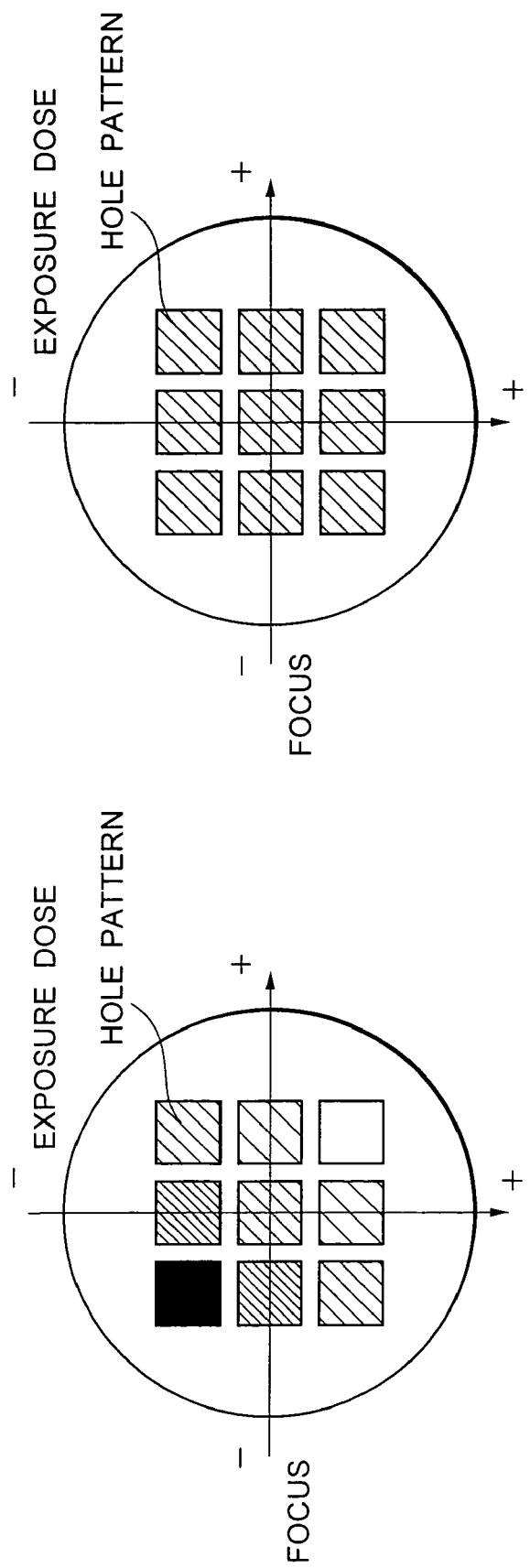

BACKGROUND OF THE INVENTION

1. Field of the Invention

The present invention relates to a defect inspection apparatus and a defect inspection method for detecting defects such as surface irregularities or dents etc. on a substrate for use, for example, in a process of manufacturing semiconductor devices or the like. The present invention also relates to a method of inspecting a hole pattern such as a contact hole or the like.

2. Related Background Art

In the manufacturing of a semiconductor device or liquid crystal substrate, various different circuit patterns are formed repeatedly in many layers. A process for forming each circuit pattern generally includes the steps of applying a resist on the surface of a substrate, exposing the resist with a circuit pattern on a reticle or a mask by means of an exposure apparatus, forming a circuit pattern of the resist by development, and then forming parts of a device by etching or a similar process. After the pattern of the resist is formed, inspection is performed to determine whether or not there is something wrong with the pattern.

FIG. 7 schematically shows a conventional inspection apparatus used for the above-described purpose. In this apparatus, a semiconductor wafer 2 placed on a stage 3 is illuminated with illumination light L1 and an image of a substrate formed by diffracted light L2 generated by a repeat pattern (not shown) formed on the semiconductor wafer 2 is picked up by an image pickup element 5. The image is processed by an image processing apparatus 6 and defects on the surface of the substrate are detected based on comparison of the obtained image with an image of a normal substrate. Since the direction in which the diffracted light emerges from the semiconductor wafer 2 varies in accordance with the pitch of the repeat pattern, the stage 3 is tilted appropriately in accordance with that pitch. As an example of such apparatus, there is Japanese Patent Application Laid-Open No. 11-51874.

Although the object to be inspected is the resist pattern formed on the uppermost layer (i.e. the outermost layer) of the semiconductor wafer 2, a part of the light that illuminates the substrate passes through the upper most resist layer to illuminate a pattern formed in an underlying layer. Therefore, the diffracted light generated by the substrate as a whole reflects not only the resist pattern of the uppermost layer but also the pattern of the underlying layer. Consequently, when the influence of the pattern of the underlying layer is significantly large, it constitutes a noise and information on the pattern of the uppermost layer that is to be primarily inspected is relatively decreased, so that a problem of deterioration of the S/N ratio arises. Especially, a hole pattern such as a contact hole pattern, which is fine and has a low pattern density, is susceptible to influence of the underlying layer, since the signal intensity is weak. For that reason, it has been impossible in the past to detect defects of a hole pattern reliably.

When an antireflection layer absorbing light used for the inspection is formed between the uppermost layer and the underlying layer, the above-described problem does not arise. However, it becomes difficult to obtain a three-dimensional information of the pattern formed on the uppermost layer.

SUMMARY OF THE INVENTION

The present invention has been made in view of the above-described situations. An object of the present invention is to provide a defect inspection apparatus, a defect inspection method and a hole pattern inspection method with which inspection of an uppermost pattern can be performed with a high S/N ratio.

According to a first aspect of the present invention, there is provided a defect inspection apparatus for inspecting a defect of a substrate as an object to be inspected, comprising, an illumination optical system for illuminating the substrate, a receiving optical system for receiving diffracted light from the substrate, and a polarizing element provided in either one of the illumination optical system or the receiving optical system.

In the case that a pattern is not formed on the surface of a substrate, the reflectance at the substrate surface is larger for S-polarized light included in the illumination light than for P-polarized light. Therefore, upon performing inspection, it is preferable to use light that includes larger S-polarized light component, since in that case the quantity of light reflected by the surface of the substrate will be larger than the quantity of light getting into the substrate and reflected by the boundary of the underlying layer and the S/N ratio can be enhanced accordingly. Although this condition may change when a pattern is formed in the substrate, there is a certain polarization state for which the reflectance at the surface of a substrate is relatively high, in any case.

According to the first aspect of the present invention, there is provided a defect inspection apparatus in which a polarizing element is provided in either one of the illumination optical system or the receiving optical system. In this apparatus it is possible to increase the polarized light component for which the reflectance is high included in the illumination light incident on the surface of the substrate or in the reflected diffracted light by adjusting the polarizing element. Therefore, inspection can be performed with a good S/N ratio accordingly.

According to a second aspect of the present invention, there is provided a defect inspection apparatus for inspecting a defect of a substrate as an object to be inspected, comprising an illumination optical system for illuminating the substrate, a receiving optical system for receiving diffracted light from the substrate, a first polarizing element provided in the illumination optical system, and a second polarizing element provided in the receiving optical system.

The defect inspection apparatus according to the second aspect of the present invention includes the first polarizing element provided in the illumination optical system and the second polarizing element provided in the receiving optical system. With this feature, it is possible to establish a state in which only such diffracted light component derived from the illumination light that has been changed in its polarization state when reflected at the substrate surface is received, by for example establishing the state of crossed Nicols between the first polarizing element and the second polarizing element. In this way, the quantity of the background light can be reduced, so that inspection can be performed with a good S/N ratio.

In addition, in the case of a substrate composed of two or more layers, the polarization state of the light reflected at the surface of the substrate is sometimes different from the polarization state of the light reflected at a layer boundary inside the substrate. In that case, it is possible to reduce the light that has been reflected at the layer boundary inside the substrate included in the received light by adjusting the two polarizing plates in such a way that the condition of crossed Nicols is set for the light reflected at the layer boundary inside the substrate. In this way the diffracted light reflected at the surface of the substrate can be detected with a good S/N ratio.

According to a third aspect of the present invention that attains the aforementioned object, in the apparatus according to the second aspect of the invention, a quarter wave plate is additionally provided between the substrate and the first polarizing element or between the substrate and the second polarizing element. With this feature, it is possible to convert the illumination light or the diffracted light into linearly polarized light in a specific direction. Therefore, it is possible to enhance the effects of the defect inspection apparatus according to the second aspect of the invention by adjusting the quarter wave plate to convert the illumination light or the diffracted light into linearly polarized light and establishing the condition of crossed Nicols for the linearly polarized light.

According to a fourth aspect of the invention that attains the aforementioned object, in the defect inspection apparatus according to any one of the first to third aspects of the invention, the apparatus is further provided with image pickup means for picking up an image of the substrate formed by the diffracted light received by the receiving optical system and an image processing apparatus for performing image processing based on an output from the image pickup means to detect a defect of the substrate.

With the provision of the image pickup means for picking up an image of the substrate utilizing the diffracted light received by the receiving optical system and the image processing apparatus for performing image processing based on an output from the image pickup means to detect a defect of the substrate, the defect inspection apparatus according to the fourth aspect of the invention can perform inspection automatically.

According to a fifth aspect of the present invention that attains the aforementioned object, there is provided a method of inspecting a surface defect of a substrate as an object to be inspected, comprising the steps of illuminating the substrate with linearly polarized illumination light, picking up an image of the substrate formed by diffracted light from the substrate, and processing the picked up image to detect a defect of the substrate. In this defect inspection method, since the substrate is illuminated with linearly polarized illumination light, it is possible to perform inspection with a good S/N ratio by selecting, for use in inspection, linearly polarized light to which the reflectance of the surface of the substrate is high.

According to a sixth aspect of the present invention that attains the aforementioned object, there is provided a method of inspecting a surface defect of a substrate as an object to be inspected, comprising the steps of, illuminating the substrate with illumination light, picking up an image of the substrate formed by certain linearly polarized light included in diffracted light from the substrate, and processing the picked up image to detect a defect of the substrate.

In this defect inspection method, since an image of the substrate formed by arbitrary linearly polarized light included in the diffracted light from the substrate is picked up, it is possible to perform inspection with a good S/N ratio by selecting linearly polarized light to which the reflectance of the surface of the substrate is high.

According to a seventh aspect of the present invention that attains the aforementioned object, in the defect inspection method according to the fifth or sixth aspect of the invention, the linearly polarized illumination light or the linearly polarized diffracted light is S-polarized light. In this method, it is possible to perform inspection with a good S/N ratio by using S-polarized light as the linearly polarized illumination light or the linearly polarized diffracted light, since the reflectance of the surface is high for S-polarized light.

According to an eighth aspect of the present invention that attains the aforementioned object, there is provided a method of inspecting a surface defect of a substrate as an object to be inspected, comprising the steps of, illuminating the substrate with linearly polarized illumination light, picking up an image of the substrate formed by certain linearly polarized light included in diffracted light from the substrate, and processing the picked up image to detect a defect of the substrate.

In this defect inspection method, the substrate is illuminated with linearly polarized illumination light and an image of the substrate formed by arbitrary linearly polarized light included in diffracted light from the substrate is picked up. Therefore, it is possible, for example, to establish a state in which only such diffracted light component derived from the illumination light that has been changed in its polarization state when reflected at the substrate surface is used as the linearly polarized light for the imaging. Thus, the quantity of the background light can be reduced, so that inspection can be performed with a good S/N ratio.

In addition, in the case of a substrate composed of two or more layers, the polarization state of the light reflected at the surface of the substrate is sometimes different from the polarization state of the light reflected at a layer boundary inside the substrate. In that case, it is possible to detect the diffracted light reflected at the surface with a good S/N ratio by converting the light reflected at the surface of the substrate into linearly polarized light and using only that polarized light for imaging.

According to a ninth aspect of the present invention that attains the aforementioned object, there is provided a method of inspecting a surface defect of a substrate as an object to be inspected, comprising the steps of, illuminating the substrate with linearly polarized illumination light, picking up an image of the substrate utilizing light remaining after certain linearly polarized light included in diffracted light from the substrate has been removed, and processing the picked up image to detect a defect of the substrate.

In this defect inspection method, the substrate is illuminated with linearly polarized illumination light and an image of the substrate is picked up utilizing light remaining after arbitrary linearly polarized light included in diffracted light from the substrate has been removed. Therefore it is possible to remove such diffracted light component derived from the illumination light that has not been changed in its polarization state when reflected at a boundary surface inside the substrate to use the remaining light for imaging. In this way, the quantity of the background light can be reduced, so that inspection can be performed with a good S/N ratio. The diffraction light as linearly polarized light may be removed, for example, by setting a polarizing plate in such a way that the condition of crossed Nicols is established.

In addition, in the case of a substrate composed of two or more layers, the polarization state of the light reflected at the surface of the substrate is sometimes different from the polarization state of the light reflected at a layer boundary in the substrate. In that case, it is possible to reduce the light that has been reflected at the layer boundary inside the substrate included in the received light by converting the light reflected at a layer boundary in the substrate into linearly polarized light and establishing the condition of crossed Nicols for that linearly polarized light. In this way the diffracted light reflected at the surface of the substrate can be detected with a good S/N ratio.

According to a tenth aspect of the present invention that attains the aforementioned object, there is provided a method of inspecting a hole pattern, in which a defect of a hole pattern formed on a surface of a substrate is detected by a defect inspection method according to any one of the fifth to ninth aspects of the invention.

Generally, hole patters such as contact holes are very small, and it is impossible for conventional inspection methods to inspect them reliably. With the method according to the tenth aspect of the invention, it is possible to reduce background noise, and inspection of hole patterns can be performed with a good S/N ratio. Especially, with application of the method according to the ninth aspect of the invention, it is possible to inspect a hole pattern while distinguishing it from an underlying pattern, so that a highly precise inspection can be performed.

BRIEF DESCRIPTION OF THE DRAWINGS

FIGS. 4Aa, 4Ab, 4Ba and 4Bb show examples of hole patterns.

FIG. 5A schematically shows an image of hole patterns picked up by a defect inspection apparatus according to the present invention.

FIG. 5B schematically shows an image of hole patterns picked up by a conventional defect inspection apparatus.

DETAILED DESCRIPTION OF THE MOST PREFERRED EMBODIMENTS

Figure 1:
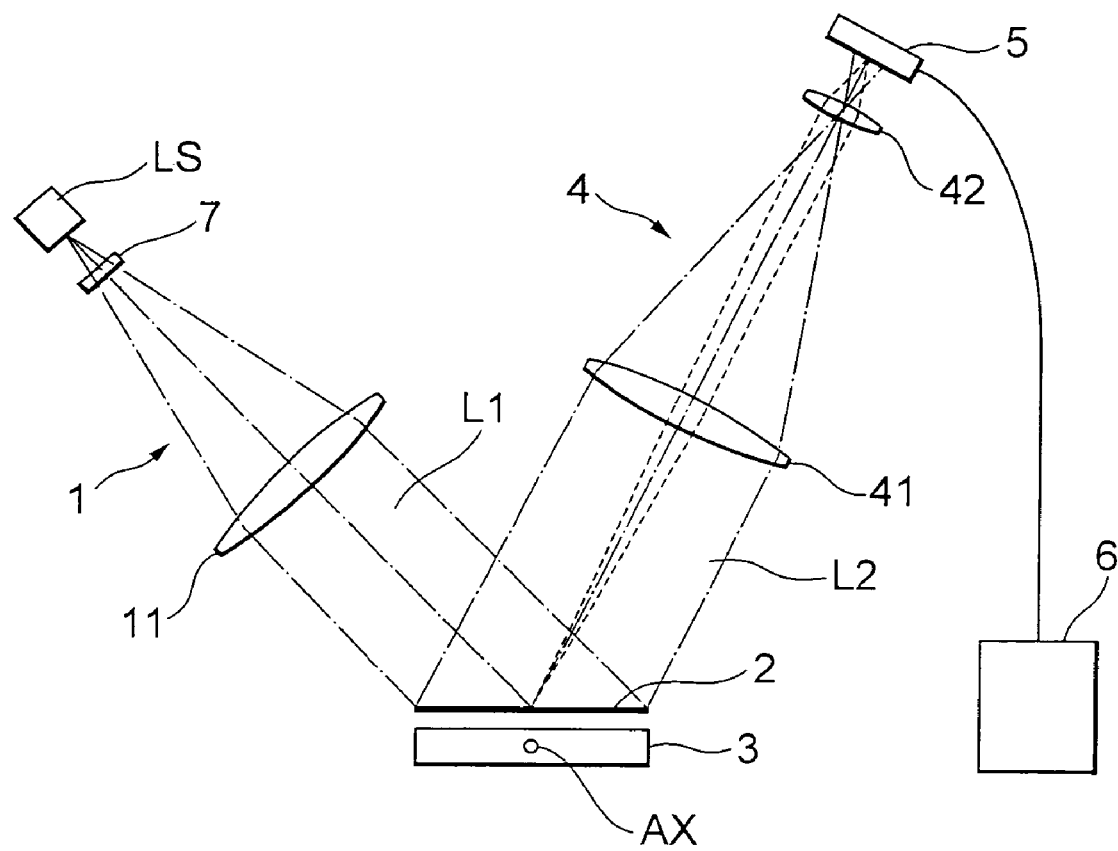
FIG. 1 schematically shows a defect inspection apparatus according to a first embodiment of the present invention.

In the following, embodiments of the present invention will be described with reference to the accompanying drawings. FIG. 1 schematically shows a defect inspection apparatus according to a first embodiment of the present invention. In this apparatus, illumination light L1 emitted from a lamp house LS is converted into substantially parallel light by a lens 11 that constitutes an illumination optical system 1 to illuminate a wafer 2 placed on a stage 3. In the interior of the lamp house LS, there is provided a light source such as a halogen lamp, a metal halide lamp or the like and a wavelength selective filter, so that light within only a limited wavelength range is picked up for use as the illumination light L1.

A polarizing plate 7 is disposed in the vicinity of light emitting portion of the lamp house LS to convert the illumination light L1 emitted from the lamp house into linearly polarized light. The polarizing plate 7 is rotatable about the optical axis of the illumination optical system 1, so that the polarization direction of the linearly polarized light that illuminates the wafer 2 can be changed arbitrarily. In addition, the polarizing plate 7 is adapted to be inserted into and removed from the optical path in the illumination optical system 1 by a certain mechanism that is not shown in the drawings. A tilt mechanism (not shown) is provided for the stage 3. The tilt mechanism is adapted to tilt the stage 3 about an axis AX that is perpendicular to the plane of the drawing sheet.

A diffracted light L2 is generated from the wafer 2 as a substrate illuminated with the illumination light. The diffraction angle of the diffracted light L2 varies depending on the pitch of a repeat pattern and the wavelength of the illumination light L1. The stage is tilted appropriately in accordance with the diffraction angle. The diffracted light L2 thus generated is directed by a receiving optical system 4 composed of lenses 41 and 42 so as to be collected. Thus, an image of the wafer 2 with the diffracted light L2 is formed on an image pickup element 5, which serves as image pickup means in the present invention. Instead of the tilting of the stage 3, the structure ranging from the lamp house LS to the illumination optical system 1 or the structure ranging from the receiving optical system 4 to the image pickup element 5 may be rotated about the axis AX. Alternatively, both the structure may be appropriately tilted in combination.

An image processing apparatus 6 performs image processing on the image picked up by the image pickup element 5. In the case that there is an abnormal state such as defocus of the exposure apparatus or a thickness irregularity in a formed pattern, a brightness difference is generated in the obtained image due to a difference in diffraction efficiency between the normal state and the abnormal state. This difference is detected as a defect by image processing. Alternatively, an image of a normal pattern may be stored in the image processing apparatus 6 in advance so that the abnormal state can be detected by determining the difference between the stored image and the measured pattern.

The diffracted light L2 is composite light including the light diffracted by the resist pattern (i.e. the upper layer pattern) at the surface of the wafer 2 and the light that is transmitted by the surface resist pattern to reach the pattern of the underlying layer (i.e. the underlying layer pattern) and diffracted at that pattern.

It is noted here that the underlying layer is not limited to a layer just or directly underlying the resist layer but includes also one or more layers positioned under or below the resist layer through one or more intervening layer(s).

The polarization plate 7 is rotationally adjusted about the optical axis in such a way that the illumination light L1 illuminates the wafer 2 as S-polarized light and an intersection between the plane of polarization of the S-polarized light and the surface of the wafer 2 becomes parallel or perpendicular to the pattern formed on the wafer 2. Here, the S-polarized light means linearly polarized light having a plane of polarization perpendicular to the plane of the drawing sheet. Incidentally, a P-polarized light means linearly polarized light having a plane of polarization parallel to the plane of the drawing sheet. Generally, the reflectance at the surface of a thin film for the light that enters that thin film from air varies depending on the refractive index of the thin film and the incidence angle of the light. In addition, the reflectance differs for P-polarized light and S-polarized light. Within the incidence angle range of 0°< to <90°, the surface reflectance for S-polarized light is higher than that for P-polarized light.

When a wafer includes a plurality of pattern layers, the quantity of light reaching the underlying layer is smaller in the case of S-polarized light than in the case of P-polarized light, since the surface reflectance for S-polarized light is higher. Consequently, the light quantity of diffracted light is also influenced by the above-described fact, and the quantity of light diffracted by the resist pattern of the upper layer as compared to the quantity of light diffracted by the pattern of the underlying layer is larger in the case of S-polarized light than in the case of P-polarized light.

Figure 2A:
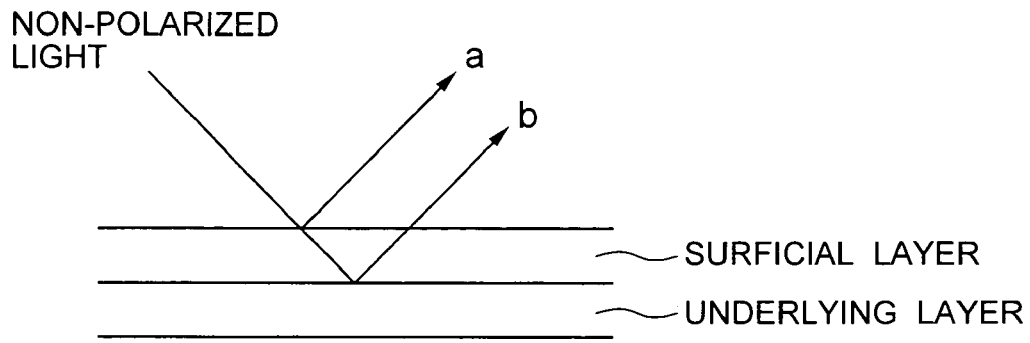
FIGS. 2A to 2C illustrate how non-polarized light, P-polarized light and S-polarized light are reflected from the surface and an underlying layer of a substrate.
Figure 2B:
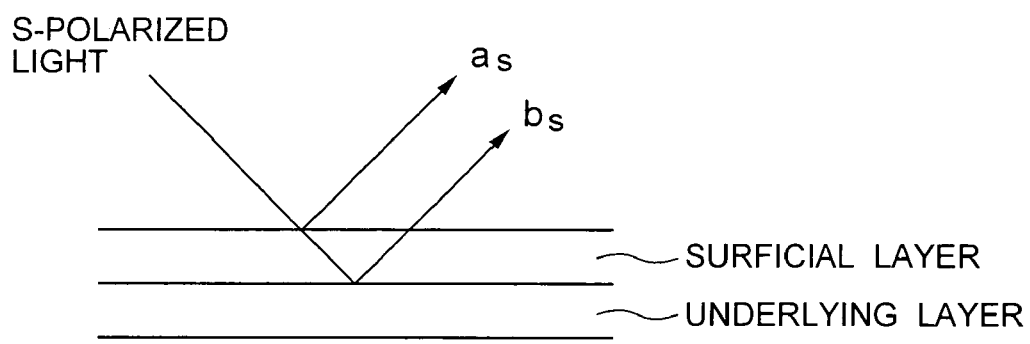
Figure 2C:
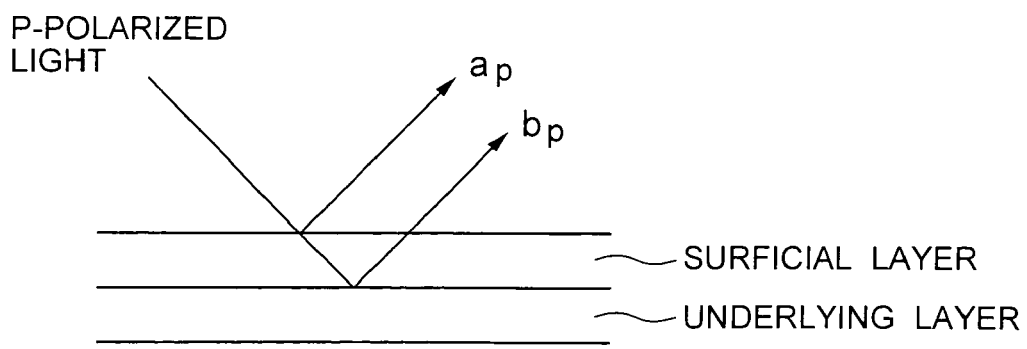

The above-described situation will be specifically described with reference to FIGS. 2A to 2C. FIGS. 2A to 2C respectively illustrate how non-polarized light, S-polarized light and P-polarized light are incident on the surface of the surficial layers and the underlying layer and reflected by them. In the case of the non-reflected light, the quantity of light reflected by the surficial layer is represented by a and the quantity of light reflected at the boundary of the surficial layer and the underlying layer is represented by b. In the case of the S-polarized light, the quantity of light reflected by the surficial layer is represented by as and the quantity of light reflected at the boundary of the surficial layer and the underlying layer is represented by $b_S$. In the case of the P-polarized light, the quantity of light reflected by the surficial layer is represented by $a_P$ and the quantity of light reflected at the boundary of the surficial layer and the underlying layer is represented by $b_P$. The magnitude relation of light quantities a, aS, aP and light quantities b, bS and bP is as follows.

$$a_P < a < a_S \text{ and}$$

$$b_P > b > b_S$$

As will be understood from the above, the quantity of light reflected at the surface of the surficial layer can be made relatively large if S-polarized light is used, so that it is possible to perform surface inspection with little influence of the underlying layer.

Incidentally, the polarizing plate 7 may be inserted in the receiving optical system, instead of in the illumination optical system, so as to pickup S-polarized light component. Such an arrangement can also realize the same effects as the arrangement in which the polarizing plate is inserted in the illumination optical system.

On the other hand, when an antireflection layer is disposed directly under the surficial layer and reflection light (diffracted light) from the underlying layer rarely exists or when a layer directly under the surficial layer is covered with a metallic layer without a pattern, the incident light is preferably P-polarized light instead of S-polarized light and the rotational position of the polarizing plate 7 is adjusted in such a way that the illumination light illuminates the wafer 2 with P-polarized light. Incidentally, the P-polarized light means linearly polarized light having a plane of polarization parallel to the plane of the drawing sheet. Although surface reflectance of the P-polarized light is lower than that of the S-polarized light, since the underlying layer does not cause noise it is no problem that the P-polarized light is incident. Since the light quantity for the P-polarized light getting into the underlying layer is larger than that for the S-polarized light, the P-polarized light has a merit to easily detect variation in the three-dimensional structure of the surficial layer pattern.

In a cross-sectional shape inspection of a hole pattern, in particular, the only way has been a destructive inspection in which a substrate is divided and observed the cross-sectional shape by a scanning electron microscope. Since the hole pattern has a low density different from a "line and space" pattern, the inspection is carried out on the basis of a very few number of a cross-sectional shape of a hole pattern corresponding to the divided-cross-sectional shape of the substrate. According to the crystal axis of the wafer and the forming direction of the hole pattern, there is a case that any one of a plurality of cross-sectional shapes of the hole patterns is not corresponding to the divided-cross-sectional shape of the substrate. As described above, observation of the cross-sectional shape of the hole pattern calls for inspector's skill in dividing the substrate, so that it has been a demanding task. According to the present invention, since variation in the three-dimensional structure of the hole pattern can be obtained by inspecting the hole pattern with the P-polarized light, the three-dimensional inspection of the hole pattern can be easily carried out nondestructively.

By the way, when the polarizing plate 7 is inserted in the receiving optical system instead of the illumination optical system and the P-polarized light is picked out from the diffracted light to be detected, the same effect as the polarizing plate is inserted in the illumination optical system is obtained.

Figure 3:
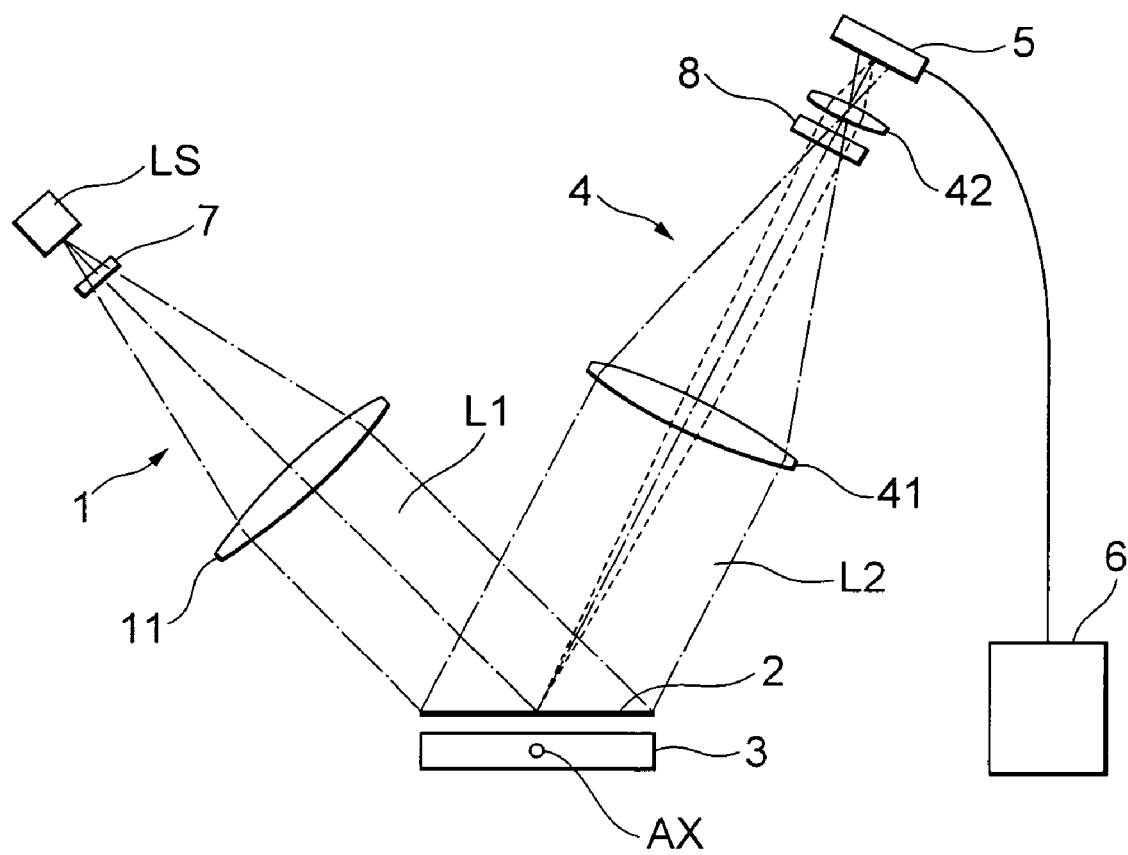
FIG. 3 schematically shows a defect inspection apparatus according to a second embodiment of the present invention.

FIG. 3 schematically shows a defect inspection apparatus according to a second embodiment of the present invention. In this and other related drawings, the parts same as or similar to the parts shown in FIG. 1 are designated by the same reference characters and the description thereof will be omitted. In the apparatus according to the second embodiment, a polarizing plate 8 is added in the receiving optical system 4 in the apparatus according to the first embodiment shown in FIG. 1. The polarizing plate 8 is rotatable about the optical axis of the receiving optical system 4. With the polarizing plate 8, it is possible to pickup linearly polarized light in an arbitrary polarizing direction included in the diffracted light L2 from the wafer 2. In addition, the polarizing plate 8 is adapted to be inserted into and removed from the optical path in the receiving optical system 4 by a certain mechanism that is not shown in the drawings.

The inventors found the fact that in the defect inspection apparatus according to the second embodiment, inspection of a hole pattern can be especially effectively performed when the wafer 2 is illuminated by linearly polarized illumination light (preferably, by illumination light having a polarization state for which the reflectance at the substrate surface is high as described before) and the polarizing plates 7 and 8 are adjusted in such a way that such linearly polarized light included in the diffracted light from the wafer that oscillates in the direction orthogonal to the illumination light L2 is picked up, namely in such a way that a state of so-called crossed Nicols is established.

Although the crossed Nicols normally renders the image field dark, areas in which hole patterns were formed could be picked up as images. This can be explained as follows. When linearly polarized light is incident on a sample, the polarization state of the light is changed when reflected and diffracted at the surface of the sample into elliptical polarization (namely, an oscillation component orthogonal to the linearly polarized incident light is generated). As a result, when the state of crossed Nicols is established, such a light component that has changed in the polarization state through the incidence on the sample can be picked up.

As going into more detail, when the polarized light incident on a pattern is assumed to be divided into two components in which one direction is parallel to the line (edge portion) direction of the pattern and the other direction is perpendicular to the line direction of the pattern, effect of deviation in reflectance and phase caused by the shape of the pattern such as pitch and duty ratio differs between the parallel component and the perpendicular component, so that the polarized light reflected from the pattern, in other words, the polarized light composed of the parallel component and the perpendicular component to the pattern after reflection differs in its shape from the incident polarized light. Accordingly, when relative position between the substrate and the illumination optical system is adjusted such that the intersection between the plane of polarization of the polarized light incident on the edge portion and the wafer plane becomes parallel or perpendicular to the direction of the pattern formed on the different layer from the hole pattern, the oscillating direction of the polarized light diffracted from the pattern rarely varies. In this case, since the oscillating direction of the polarized light incident on the edge portion is parallel or perpendicular to the pattern, the oscillation component of the polarized light only exists in the direction parallel or perpendicular to the line direction of the pattern, so that the oscillation direction does not vary in accordance with the pattern. On the other hand, since a hole pattern is a circular pattern, the relation between the oscillation direction of the incident linear polarized light and the direction of the edge portion differs at respective edge portions of the hole pattern (the polarized light is incident on the edge portion with making an angle between the plane of polarization and the edge direction neither parallel nor perpendicular with each other). Accordingly, a light signal from the hole pattern among the light diffracted from the hole pattern can be picked out in the manner without causing decrease, so that it becomes possible to separate a pattern disposed under the hole pattern.

As for the crossed Nicols combination, there are two cases in which one is that S-polarized light is incident as the illumination light and P-polarized component is picked out among the diffracted light from the wafer and the other is that P-polarized light is incident as the illumination light and S-polarized component is picked out among the diffracted light from the wafer. When an influence from an underlying layer is to be suppressed as much as possible, the former case is suitable. When variation in a three-dimensional structure of a hole pattern is to be effectively obtain, the latter case is suitable. In each case, polarizing plates 7 and 8 are suitably adjusted.

In this case also, since the influence of the underlying layer can be kept small, the inspection of the hole pattern is carried out by using P-polarized light and by obtaining variation in a three-dimensional structure of a hole pattern, the three-dimensional inspection of the hole pattern can be easily carried out nondestructively.

The amount of change in the polarization state generated upon diffraction at the hole pattern of the upper layer is much larger than the amount of change generated upon diffraction at the pattern of the underlying layer. Therefore, information of the upper layer pattern can be detected efficiently by focusing on the change in the polarization state, even when the quantity of light diffracted at the underlying layer pattern is larger than the quantity of light diffracted at the upper layer pattern.

Examples of hole patterns are shown in FIGS. 4Aa, 4Ab, 4Ba and 4Bb. FIGS. 4Aa and 4Ab show a pattern 21 constituting the underlying layer and contact holes 22 formed on it, where FIG. 4Aa is a plan view and FIG. 4Ab is a cross sectional view taken along line A-A in FIG. 4Aa. FIGS. 4Ba and 4Bb show an insulating layer 25 constituting the underlying layer and contact holes 22 formed on it, where FIG. 4Ba is a plan view and FIG. 4Bb is a cross sectional view taken along line A-A in FIG. 4Aa.

In FIGS. 4Aa and 4Ab, the pattern 21 is formed on a substrate 24 and the contact holes 22 are formed on the pattern 21 in a predetermined hole pattern. The portion on which the pattern 21 is not formed is covered with resist 23. In addition, the portion of the pattern 21 on which the contact holes 22 are not formed is also covered with the resist 23.

In FIGS. 4Ba and 4Bb, the pattern 21 is formed on the substrate 24, the portion on which the pattern 21 is not formed and the pattern 21 are covered with the insulation layer 25. The contact hole 22 is formed with a predetermined pattern arrangement through the insulation layer 25.

In FIGS. 4Aa and 4Ab, the pattern 21 is formed just below the contact holes or hole patterns 22, and the pattern density of the pattern 21 is larger than that of the hole patterns 22.

The pattern 21 is made from metal having generally high light reflective index such as copper or aluminum, while the resist layer 23 is made from transparent organic compound such as polyhydroxy styrene. Accordingly, the intensity of light diffracted at the contact holes or hole patterns 22 formed in the resist layer 23 is smaller than that of light having passed the resist layer 23 and being diffracted by the pattern 21, so signal of the diffraction light diffracted by the contact holes or hole patterns 22 would be buried in that of diffraction light diffracted by the pattern 21.

For such reason, it was not possible to detect a signal of the diffraction light from the contact holes or hole patterns 22.

In FIGS. 4Ba and 4Bb, on a substrate 24 the pattern 21 is formed, and thereon the insulating layer 25 is formed. On the insulating layer 25, the resist layer 23 is formed on which the contact holes 22 is formed in a predetermined pattern arrangement. Since the insulating layer 25 is generally made of transparent SiO2, light passing through the resist layer 23 reaches the pattern layer 21 without being absorbed in the insulating layer 25. Thus, light having passed through the resist layer 23 and the insulating layer 25, reaches the pattern layer 21 and is diffracted thereby to generate diffraction light.

In this case also, similar to the case in FIGS. 4Aa and 4Ab, the intensity of the diffraction light from the contact holes or hole patterns 22 formed in the resist layer 23 is smaller than that of the light which has passed through the resist layer 23 and has been diffracted by the pattern 21, so a signal of the diffraction light diffracted by the contact holes or hole patterns 22 would be buried in a signal of the diffraction light diffracted by the pattern 21. Therefore, even if the insulating layer 25 is formed on the pattern 21, it is not possible to detect the signal of the contact holes or hole patterns 22.

The inventors prepared a substrate having a structure as shown in FIGS. 4Aa and 4Ab, and comprising a wafer, a pattern formed thereon, the pattern being made of aluminum and having a defect-free repeated pattern, a resist layer formed just thereon, and contact holes or hole patterns made in the resist layer by making exposure while varying focus amount and exposure dose with the exposure condition with the best focus and the best exposure does being the center of variation.

Although perfect hole patterns were formed under the best focus and best exposure dose condition, defects in hole patterns were generated as the condition changes away from the best focus and exposure dose condition.

Figure 7:
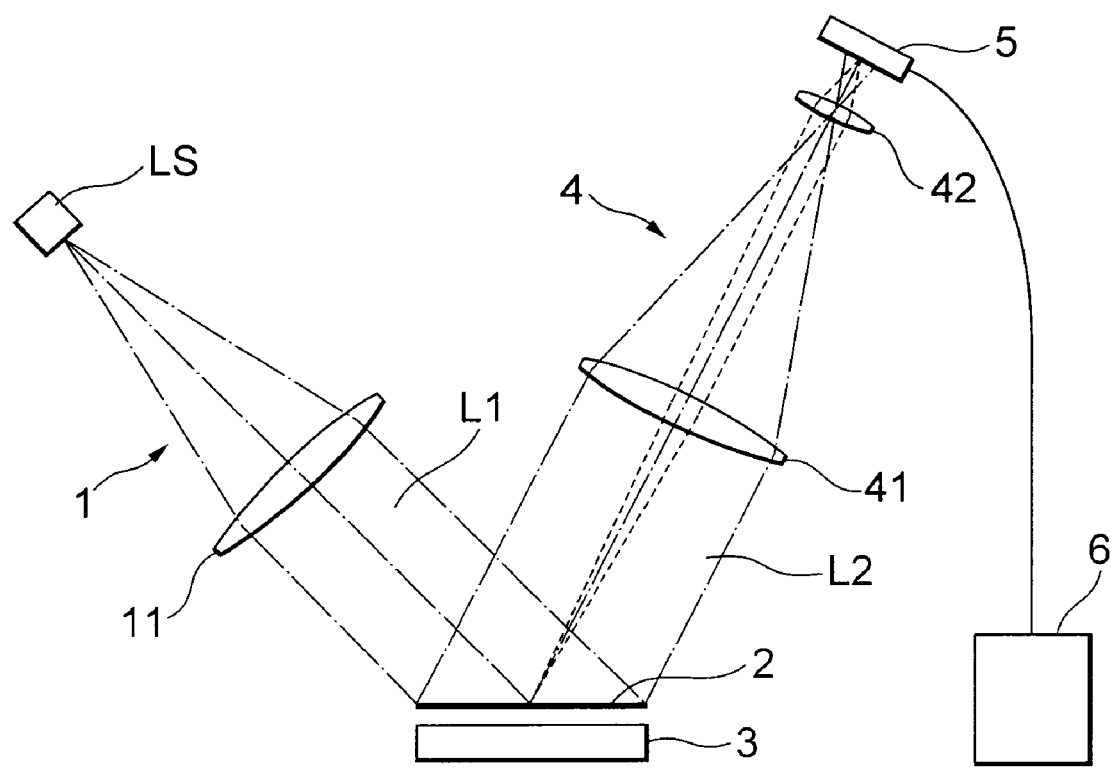
FIG. 7 schematically shows a conventional defect inspection apparatus.

We picked up an image of the various hole patterns thus formed on the wafer using a conventional inspection apparatus shown in FIG. 7.

FIG. 5B schematically shows the picked-up image. As shown in FIG. 5B, there are nine hole patterns corresponding to different exposure conditions formed on one wafer, and the brightness of the respective picked-up images are schematically shown in FIG. 5B. In the patterns shown in FIG. 5B, the hole pattern at the center was formed by exposure with the best focus and the best exposure dose. The patterns in the right column were formed by exposure in which the focus position was displaced in the plus direction along the optical axis, and the patterns in the left column were formed by exposure in which the focus position was displaced in the minus direction along the optical axis. The patterns in the lower row were formed by exposure in which the exposure dose was varied by a plus amount, and the patterns in the upper row were formed by exposure in which the exposure dose was varied by a minus amount.

As shown in FIG. 5B, the variation of the hole patterns could not be detected as a difference in the brightness of the shot areas due to influence of diffracted light from the repeat pattern of the underlying layer. Thus, the picked-up images of all of the hole patterns had the same brightness.

We also measured the same wafer using the inspection apparatus shown in FIG. 3 under the condition in which the cross Nicol condition was met for diffracted light from the underlying layer of the hole pattern. FIG. 5A schematically shows the picked-up image. In this image, diffracted light from the underlying repeated pattern had been eliminated and the variation in the focus amount and the exposure dose of the exposure apparatus was detected as a variation in the brightness of the hole pattern areas as shown in FIG. 5A.

The diameter of holes varies with a variation in the focus amount and the exposure dose. This causes a variation in diffraction efficiency, which, in turn, causes a variation in the image brightness. The variation in the brightness can be satisfactorily detected by image processing, and therefore defects in a hole pattern caused by defocus or insufficiency of exposure dose in the exposure apparatus can be detected.

Figure 6:
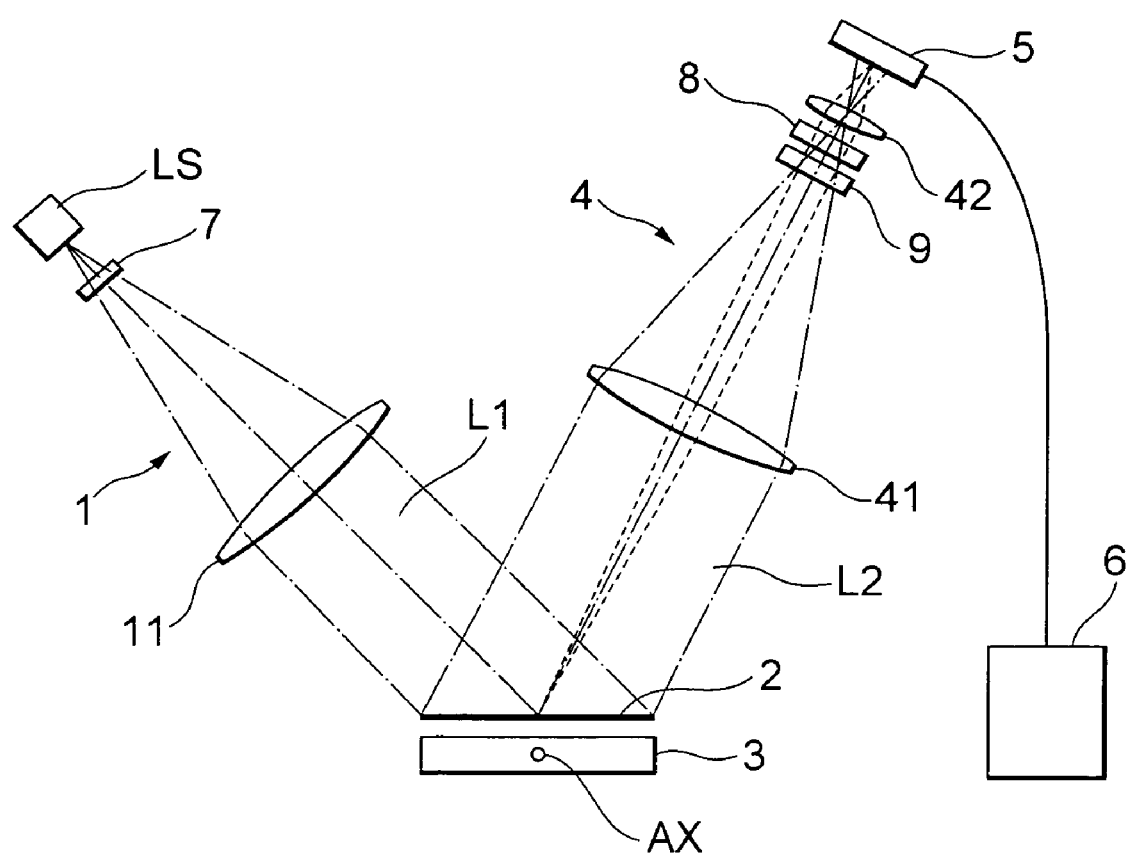
FIG. 6 schematically shows a defect inspection apparatus according to a third embodiment of the present invention.

FIG. 6 schematically shows a defect inspection apparatus according to a third embodiment of the present invention. This embodiment differs from the second embodiment in that a quarter wave plate 9 is disposed between the polarizing plate 8 and the wafer 2 in the receiving optical system 4. The quarter wave plate 9 is rotatable about the optical axis of the receiving optical system and adapted to be inserted into and removed from the optical path of the receiving optical system 4. As well known, the quarter wave plate has a function of changing the polarization state of incident light into linear polarization, elliptic polarization or circular polarization in accordance with the rotational position.

As described before, the diffracted light L2 is composite light composed of diffracted light diffracted at the upper layer pattern and diffracted light diffracted at the underlying layer pattern. The polarization states of the respective light components are different from each other. In view of this fact, the rotational position of the quarter wave plate 9 is adjusted in such a way as that it converts the diffracted light from the underlying layer into linearly polarized light, and the rotational position of the polarizing plate 8 is adjusted in such a way that the light that oscillates in the direction perpendicular to the oscillation direction of the linearly polarized light thus converted is picked up, namely, in such a way that a state of crossed Nicols is established. With the above-described adjustment, the diffracted light from the underlying layer is removed. In connection with this, the diffracted light from the upper layer after passing through the quarter wave plate 9 is not linearly polarized light, though the polarization state thereof has been changed by the quarter wave plate 9, and therefore it can pass through the polarizing plate 8. In this way, the light that has passed through the polarizing plate 8 includes only the diffracted light from the upper layer and the diffracted light from the underlying layer has been removed. Therefore, inspection can be performed with a good S/N ratio without influence from the underlying layer.

The quarter wave plate may be inserted between the polarizing plate 7 and the wafer 2 in the illumination optical system 1 instead of in the receiving optical system 4. In this case also, it is possible to convert the diffracted light from the underlying layer included in the light diffracted by the wafer 2 into linearly polarized light. Thus, the same effects as in the case that the quarter wave plate is inserted in the receiving optical system are realized.

As has been described in the foregoing, the present invention can provided a defect inspection apparatus, a defect inspection method and a hole pattern inspection method with which inspection of a pattern on an uppermost layer can be performed with a high S/N ratio.

What is claimed is:

1. A defect inspection apparatus for inspecting a defect of repeated patterns formed as a top layer of a substrate on which a plurality of layers of repeated patterns are formed, comprising:

an illumination optical system for illuminating the repeated patterns formed as the top layer of the substrate on which a plurality of layers of repeated patterns are formed; and a receiving optical system for receiving diffracted light from the substrate;

wherein a first polarizing element is provided in the illumination optical system and a second polarizing element is provided in the receiving optical system such that the second polarizing element forms a crossed Nicols relation with the first polarizing element; and the first polarizing element disposed so that an intersection line of a plane of oscillation of polarized light exited from the first polarizing element with the substrate is made substantially parallel or perpendicular to a direction of repetition of patterns of a layer that is lower than the repeated patterns.

2. A defect inspection apparatus according to claim 1 further comprising a quarter wave plate provided between said substrate and said first polarizing element or between said substrate and said second polarizing element.

3. A defect inspection apparatus according to claim 2 further comprising an image pickup means for picking up an image of said substrate formed by said diffracted light received by said receiving optical system and an image processing apparatus for performing image processing based on an output from said image pickup means to detect a defect of said substrate.

4. A defect inspection apparatus according to claim 1 further comprising an image pickup means for picking up an image of said substrate formed by said diffracted light received by said receiving optical system and an image processing apparatus for performing image processing based on an output from said image pickup means to detect a defect of said substrate.

5. A method of inspecting a surface defect of repeated patterns formed as a top layer of a substrate on which a plurality of layers of repeated patterns are formed as an object to be inspected, comprising the steps of:

illuminating with linearly polarized illumination light the repeated patterns formed as the top layer of the substrate on which a plurality of layers of repeated patterns are formed;

picking up linearly polarized light component whose direction of polarization is perpendicular to that of said linearly polarized illumination light among diffracted light of elliptic polarization component from the substrate;

taking an image of the repeated patterns formed by said linearly polarized light component; and processing the taken image to detect a defect of the repeated patterns formed as the top layer of the substrate, wherein an intersection line of a plane of oscillation of the linearly polarized light with the substrate is substantially parallel or perpendicular to a direction of repeated patterns of a layer that is lower than the repeated patterns.

6. A method of inspecting a hole pattern, in which a defect of a hole pattern formed on a surface of a substrate is detected by a defect inspection method according to claim 5.

7. A defect inspection apparatus for inspecting a defect of repeated patterns formed as a top layer of a substrate on which a plurality of layers of repeated patterns are formed, comprising:
- an illumination optical system for illuminating with P-polarized light illumination light the repeated patterns formed as the top layer of the substrate on which a plurality of layers of repeated patterns are formed; and
- a receiving optical system for receiving S-polarized light among diffracted light of elliptic polarization component from the substrate, wherein an intersection line of a plane of oscillation of the p-polarized light with the substrate is substantially parallel or perpendicular to a direction of repeated patterns of a layer that is lower than the repeated patterns.

8. The defect inspection apparatus according to claim 7, wherein a defect to be detected is a defect of a hole pattern formed on a surface of said substrate.

* * * * *

UNITED STATES PATENT AND TRADEMARK OFFICE
CERTIFICATE OF CORRECTION

PATENT NO. : 7,643,137 B2　　　　　　　　　　　　　　　　　　　　　Page 1 of 1
APPLICATION NO. : 11/243425
DATED : January 5, 2010
INVENTOR(S) : Sugihara et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 324 days.

Signed and Sealed this

Sixteenth Day of November, 2010

David J. Kappos
*Director of the United States Patent and Trademark Office*